US011998763B2

(12) United States Patent
Matteo et al.

(10) Patent No.: US 11,998,763 B2
(45) Date of Patent: Jun. 4, 2024

(54) ENERGY SELECTION SYSTEM FOR COMPACT PROTON THERAPY

(71) Applicant: ProNova Solutions, LLC, Maryville, TN (US)

(72) Inventors: Joseph C Matteo, Walland, TN (US); Vladimir Derenchuk, Maryville, TN (US); Ron Moore, Knoxville, TN (US); Jacob Shamblin, Hendersonville, TN (US); Aaron Jacques, Knoxville, TN (US)

(73) Assignee: ProNova Solutions, LLC, Maryville, TN (US)

( * ) Notice: Subject to any disclaimer, the term of this patent is extended or adjusted under 35 U.S.C. 154(b) by 0 days.

(21) Appl. No.: 17/845,272

(22) Filed: Jun. 21, 2022

(65) Prior Publication Data
US 2022/0401759 A1    Dec. 22, 2022

Related U.S. Application Data

(60) Provisional application No. 63/212,940, filed on Jun. 21, 2021.

(51) Int. Cl.
*A61N 5/10*    (2006.01)
*H05H 7/04*    (2006.01)

(52) U.S. Cl.
CPC .......... *A61N 5/1077* (2013.01); *H05H 7/04* (2013.01); *A61N 2005/1087* (2013.01)

(58) Field of Classification Search
CPC ............... A61N 5/1077; A61N 2005/1087
See application file for complete search history.

(56) References Cited

U.S. PATENT DOCUMENTS

| 2009/0050819 | A1 | 2/2009 | Ma et al. |
| 2011/0101236 | A1* | 5/2011 | Cameron ............ A61N 5/1077 |
| | | | 250/396 ML |
| 2015/0087884 | A1 | 3/2015 | Huber et al. |
| 2017/0368373 | A1* | 12/2017 | Sahadevan .......... A61M 1/3615 |
| 2017/0372867 | A1* | 12/2017 | Caspi ....................... H01F 6/06 |
| 2019/0108965 | A1 | 4/2019 | Papeer et al. |
| 2019/0151677 | A1 | 5/2019 | Jongen |

(Continued)

FOREIGN PATENT DOCUMENTS

WO    WO2021113323 A1    6/2021

OTHER PUBLICATIONS

Patent Cooperation Treaty, PCT International Search Report, Form PCT/ISA/220, dated Oct. 5, 2022.

*Primary Examiner* — Eliza W Osenbaugh-Stewart
(74) *Attorney, Agent, or Firm* — Pitts Lake, LLC (57) ABSTRACT

A proton treatment system including a proton accelerator structured to generate a proton beam, a beamline pathway configured to direct the proton beam from the proton accelerator to at least one treatment room, a magnet assembly, including superconducting magnets, located in the beamline pathway and configured to transport the proton beam away from the accelerator into the at least one treatment room, an achromat, configured as an achromatic superconducting magnet assembly, that bends the proton beam away from the proton accelerator toward the at least one treatment room, and a collimator provided inside the achromat and configured to select the proton beam with desired energy levels.

3 Claims, 3 Drawing Sheets

(56) References Cited

U.S. PATENT DOCUMENTS

| | | |
|---|---|---|
| 2020/0215353 A1 | 7/2020 | Song et al. |
| 2020/0306561 A1 | 10/2020 | Huggins et al. |
| 2020/0316408 A1 | 10/2020 | Jacques et al. |
| 2021/0299480 A1* | 9/2021 | Sasai ................ A61N 5/103 |

* cited by examiner

ENERGY SELECTION SYSTEM FOR COMPACT PROTON THERAPY

CROSS-REFERENCE TO RELATED APPLICATIONS

This application claims the benefit of U.S. Provisional Patent Application Ser. No. 63/212,940, filed on Jun. 21, 2021, which is incorporated herein in its entirety by reference.

FIELD OF INVENTION

The present general inventive concept relates to a proton therapy system, and, more particularly, to a compact beamline proton therapy system with a collimator located in an assembly of superconducting magnets designed to bend the protons away from the accelerator and towards a treatment room and an energy selection system to selectively control energy of the proton beam.

BACKGROUND

Proton Therapy (PT) is a cancer treatment technology that uses high energy protons to penetrate a patient's body and deposit energy into treatment areas such as cancerous tumors. Conventional PT systems typically implement a proton accelerator that produces a high energy beam that is delivered to a treatment area through a long and complicated beamline. However, one of the challenges facing current proton therapy is the high cost and size requirements for such systems, which inhibits this effective type of therapy from becoming widely used and accepted. As such, it would be desirable to provide a proton therapy system that is able to be more compactly implemented to reduce project and equipment costs.

BRIEF SUMMARY

According to various example embodiments of the present general inventive concept, a proton treatment system is provided to direct a generated proton beam along a beamline pathway from a proton accelerator to at least one treatment room. In various example embodiments a bidirectional superconducting magnet may selectively bend the proton beam to first or second beam paths so as to deliver the proton beam to different treatment rooms.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by providing a proton treatment system, including a proton accelerator structured to generate a proton beam, a beamline pathway configured to direct the proton beam from the proton accelerator to at least one treatment room, a magnet assembly, including superconducting magnets, located in the beamline pathway and configured to transport the proton beam away from the accelerator into the at least one treatment room, an achromat, configured as an achromatic superconducting magnet assembly, that bends the proton beam away from the proton accelerator toward the at least one treatment room, and a collimator provided inside the achromat and configured to select the proton beam with the desired energy levels.

The foregoing and/or other aspects and advantages of the present general inventive concept may also be achieved by providing a superconducting achromatic bend to be used in a proton therapy system, the superconducting achromatic bend including an outer vacuum chamber containing a combination of dipole and quadrupole magnets, and at least one collimator centrally located in the combination of dipole and quadrupole magnets inside the outer vacuum chamber. The combination of dipole and quadrupole magnets may include a first combination of superconducting dipole and quadrupole magnets configured at a proton beam entry point of the combination of dipole and quadrupole magnets, and a second combination of superconducting dipole and quadrupole magnets configured at a proton beam exit point of the combination of dipole and quadrupole magnets, wherein the collimator is configured between the first and second combinations of superconducting dipole and quadrupole magnets.

The foregoing and/or other aspects and advantages of the present general inventive concept may also be achieved by providing an achromatic superconducting magnet assembly to selectively bend a proton beam away from a proton accelerator toward first and second treatment rooms, including an outer vacuum chamber configured with a proton beam entry point, a first beam path leading to a first proton beam exit point, and a second beam path leading to a second proton beam exit point pointing in a direction different from the first proton beam exit point, and a bidirectional superconducting magnet unit configured proximate the proton beam entry point to selectively bend the proton beam to the first or second beam path, wherein each of the first and second beam paths include a first combination of superconducting dipole and quadrupole magnets configured to receive the proton beam from bidirectional the superconducting magnet unit, a second combination of superconducting dipole and quadrupole magnets configured to transmit the proton beam out of the achromatic superconducting magnet assembly, and a collimator configured between the first and second combinations of superconducting dipole and quadruple magnets and configured to select the proton beam with desired energy levels.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept provide a proton therapy system having a compact beamline in which a collimator is centrally located in an assembly of superconducting magnets forming an achromatic or partially achromatic bend. This assembly of magnets and collimator are co-located inside an outer vacuum chamber. In order to select a desired energy range of the proton beam, the aperture size of the collimator may be selectively adjusted. In various example embodiments, such an energy selection may be made by changing out fixed apertures, or by automated or manual adjustment of moving apertures. Such moving apertures may include, for example, moving mandibles, an iris mechanism, fluid constriction, and so on. Thus, example embodiments may provide a superconducting achromatic bend with collimation centrally located in the chain and within the superconducting chamber. In various example embodiments initial collimation of the proton beam may occur before the proton beam reaches the bending magnets in the superconducting chamber. In various example embodiments one or more degraders and/or superconducting or normal conducting quadrupoles or other magnets may be placed upstream of the outer vacuum chamber.

Such collimation of the proton beam inside the achromatic bend allows the achromatic bend to be very compact, and thus having a much smaller footprint. Without the collimator configuration of the present general inventive concept, the assembly of superconducting magnets would have to be split into multiple outer vacuum chambers, requiring more or stronger focusing magnets and collimators that require independent vacuum chambers, which takes up much more room. Thus, collimating the proton beam inside the achromatic bend helps select a desired energy of the beam, and saves space in the overall beamline. The collimation of the proton beam changes the energy range of the proton beam by trimming out any unwanted higher or lower energy protons at the center of the achromat where the energy dispersion is largest, thus tightly controlling the proton beam energy and energy range sent to a patient in the treatment area. Energy dispersion is the parameter that describes how widely the energies of the proton beam are spread horizontally, much like a prism spreading the spectral colors of light. Collimation of the protons to select the correct energy and energy range is used to prevent the proton beam from hitting depths of the patient that are outside the target area in the case of a tightly collimated beam, or to spread the protons uniformly in the patient in the case of a loosely collimated beam. As the proton beam is intercepted on the collimator located in the achromatic bend, a large heat load is produced, and thus various example embodiments of the present general inventive concept may include a variety of heat exchanging devices/methods to disperse the heat generated at the collimator.

Conventional superconducting achromat arrangements have typically included 3 superconducting quadrupoles, configured in a short-long-short layout. An achromatic bend of the present general inventive concept may include two short superconducting quadrupoles located upstream of the collimator, and two short superconducting quadrupoles located downstream of the collimator. In example embodiments that include a degrader upstream of the achromatic bend, the degrader scatters the beam and may require further heat dispersal devices/systems to deal with the heat generated at the degrader. In various example embodiments the degrader may be configured as two blocks that reduce the energy of the proton beam, but also create dispersion of energies coming out of the downstream side of the degrader. Some example systems may include another collimator placed upstream of the first dipole of the achromatic bend to trim the dispersed energy from the degrader. This upstream collimator can absorb the beam scatter that would not get through to the collimator inside the achromatic bend. Such features help to maintain the temperature inside the superconducting magnet.

Figure 1:
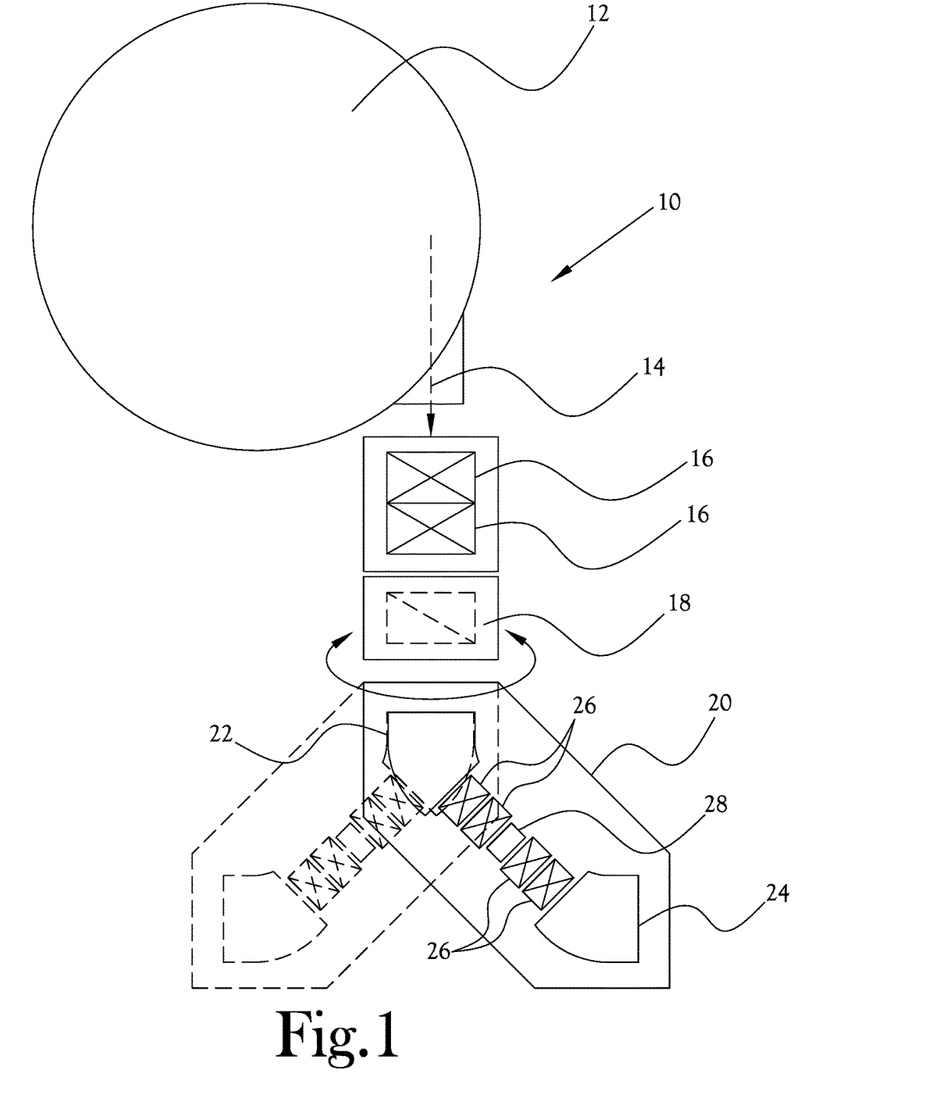
FIG. 1 illustrates a portion of a compact proton therapy system according to an example embodiment of the present general inventive concept.

FIG. 1 illustrates a portion of a compact proton therapy system according to an example embodiment of the present general inventive concept. As illustrated in FIG. 1, the compact proton therapy system 10 includes a proton accelerator 12 configured to generate a proton beam 14 to be used in the proton treatment. For the sake of clarity, the proton beam 14 is only partially illustrated in FIG. 1, as the beam 14 leaves the proton accelerator 12 and passes to a pair of superconducting or normal conducting quadrupoles 16. A degrader 18 is provided downstream from the quadrupoles 16 to partially degrade the beam before the beam enters the outer vacuum chamber housing the achromatic bend 20. In various example embodiments, one or more additional collimators may be located downstream of the degrader 18, and upstream of the achromatic bend 20. As illustrated in FIG. 1, the achromatic bend 20 includes a first dipole 22 arranged proximate a beam entry point of the achromatic bend 20, and a second dipole 24 arranged proximate a beam exit point of the achromatic bend 20. Two pairs of superconducting quadrupoles 26 are respectively provided proximate each of the first and second dipoles 22,24, and a collimator 28 is provided between the two pairs of superconducting quadrupoles 26. As illustrated in FIG. 1, all of the first and second dipoles 22,24, superconducting quadrupoles 26, and collimator 28 are located in the outer vacuum chamber of the achromatic bend 20. In various example embodiments the collimator 28 may be configured with a fixed aperture and may be interchangeable so that a particular aperture size may be provided to produce the desired energy range of the proton beam delivered to the treatment area. In other various example embodiments the collimator 28 may be configured to have a movable aperture, which may be equipped with the aforementioned moving mandibles or other elements, an iris type of mechanism, a fluid constriction arrangement, and so on, such that the collimator 28 may be adjusted to provide the desired energy level of the proton beam. In various example embodiments one or more heat transfer or otherwise dissipating elements may be provided inside the housing of the achromatic bend 20 to deal with the heat produced at the collimator 28. It is noted that different configurations and/or quantities of the elements illustrated in FIG. 1 may be employed without departing from the scope of the present general inventive concept. In addition, the assembly of superconducting magnets may be achromatic or any other arrangement provided the energy dispersion is large at the collimator. As illustrated in FIG. 1, the achromatic bend 20 may be configured to be rotatable, generally about the axis of the entering proton beam, so that the proton beam may be delivered to two or more treatment rooms. For example, as illustrated in FIG. 1, the achromatic bend 20 is configured to be selectively rotated 180 degrees so as to switch the delivery of the proton beam from a first treatment room to a second treatment room. Various example embodiments of the present general inventive concept may be configured to rotated different quantities of degrees to selectively deliver the proton beam to a plurality of different treatment rooms. Various different rotation mechanisms or assemblies may be used to rotate the achromatic bend 20 without departing from the scope of the present general inventive concept.

According to various example embodiments of the present general inventive concept, the compact beamline can be centered upon superconducting technology, reducing the overall footprint of the proton therapy system. While the terms accelerator or proton accelerator may be used in the various descriptions herein, it will be understood that a variety of different proton accelerators may be used without departing from the scope of the present general inventive concept. For example, various example embodiments of the proton therapy system may include a superconducting cyclotron (SCIC), a synchrotron, a superconducting or normal conducting synchrocyclotron, a superconducting or normal conducting isochronous cyclotron, an ironless cyclotron of any type, a fixed-field alternating gradient accelerator (FFAG), a linear accelerator, or any other accelerator that produces protons with sufficient energy for proton therapy.

Figure 2:
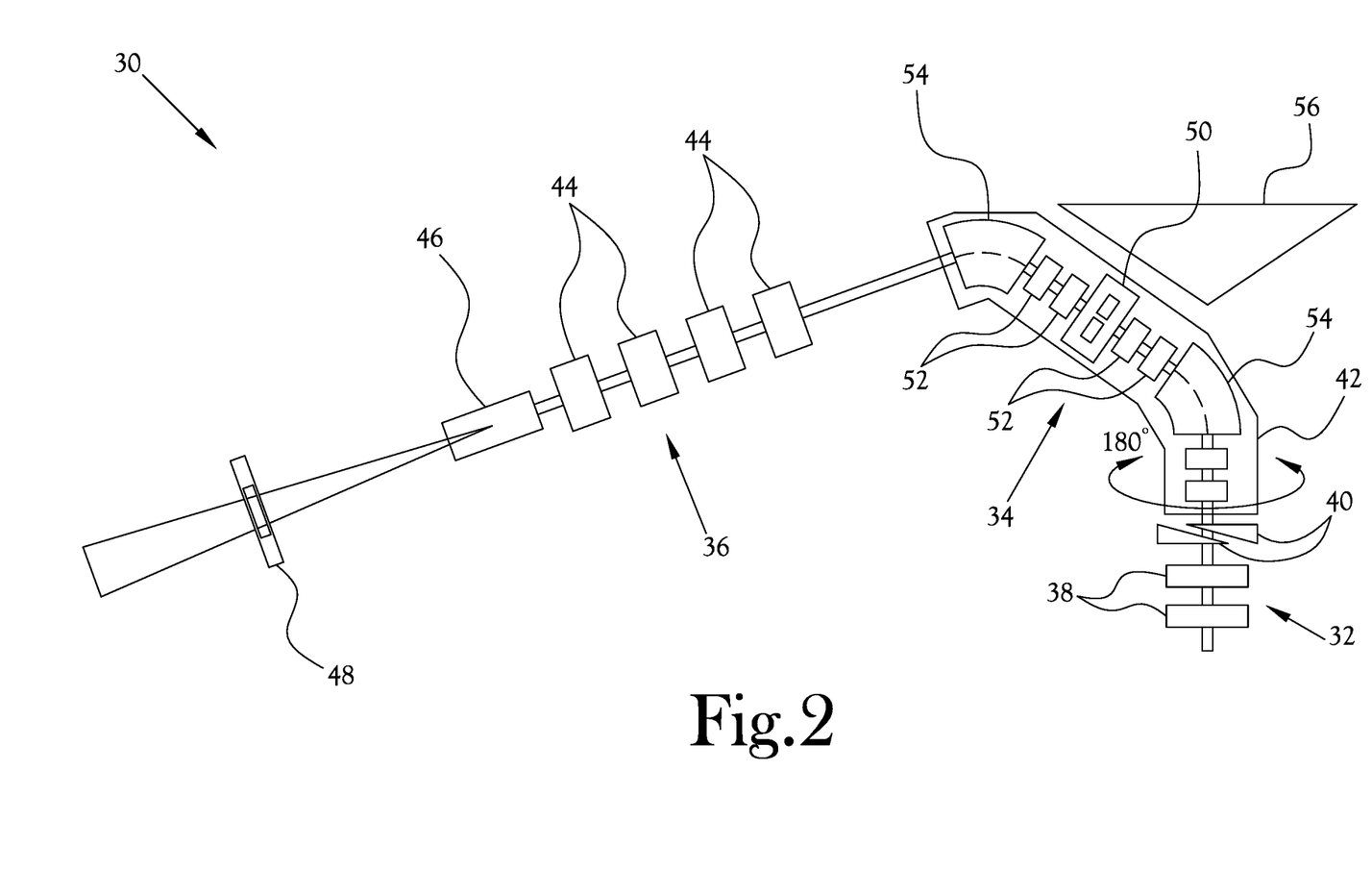
FIG. 2 illustrates a portion of a superconducting energy selection beamline according to another example embodiment of the present general inventive concept.

FIG. 2 illustrates a portion of a superconducting energy selection beamline 30 according to another example embodiment of the present general inventive concept. The superconducting energy selection beamline 30 of the treatment system may comprise three sections: an extraction beamline (EXTBL) 32, including a focusing doublet 38; an SC achromat beamline (SCABL) 34, including an achromatic bend 42 configured to rotate 180 degrees in order to send a proton beam to multiple treatment rooms; and a normal conducting beamline (NCBL) 36, including warm beamline elements as well as optional patient specific collimation 48. As illustrated in FIG. 2, while the achromatic bend 42 may be rotatable 180 degrees to deliver the proton beam to different rooms, the proton beam may be bent further than 90 degrees (such as, for example, 110 degrees) to be delivered to a room with a longer beam path than would be configured for a treatment room that is 90 degrees rotated from the proton beam delivered to the achromatic bend 42. As illustrated in FIG. 2, the achromatic bend 42 includes a collimator 50 provided between two pairs of superconducting quadrupoles 52 to help select the desired energy of the proton beam. A pair of degrader wedges making up a degrader 40 are provided between the focusing doublet 38 and the rotating achromatic bend 42, and a high density shield 56 is provided proximate the rotating achromatic bend 42. In some embodiments the EXTBL 32 can deliver a proton beam out of an SCIC onto the degrader 40 at a fixed energy of 230 MeV; the SCABL 34 can be an achromatic bend 42 made up of SC dipole and quadrupole magnets 54, 52, and the NCBL can include 4 normal conducting quadrupoles 44 and a compact multi-mode scanning magnet 46. An example embodiment using an SCIC design can generate a proton beam at a fixed energy of 230 MeV, and the degrader 40 can modulate the proton beam energy to change the penetration depth, for example from 4 to 32 cm of range in water. Other example embodiments may employ, for example, a fixed 195 MeV or fixed 250 MeV cyclotron, or anything in between, and so on, or the previously mentioned isochronous cyclotron, or synchrocyclotron, etc. The EXTBL 32 can focus and center the beam onto the degrader 40 and provide the maximum beam transmission to the downstream beamline. The achromatic bend SCABL 34 can select and transport the proton beam of the right energy and emittance to NCBL 36 for final beam focusing and wide field scanning; essential for precise treatments. Because neutron fluxes generated in the degrader 40 are perpendicular to the downstream beamline, unwanted neutron radiation to patients will be minimized. To reduce the amount of shielding, the system can include independent degraders disposed in each treatment room downstream of the switching magnet, but it is possible to use a single degrader disposed proximate an outlet of the accelerator upstream of the switching magnet. The proton therapy system can be configured in shape and size to fit within an existing two LINAC vault.

Figure 3:
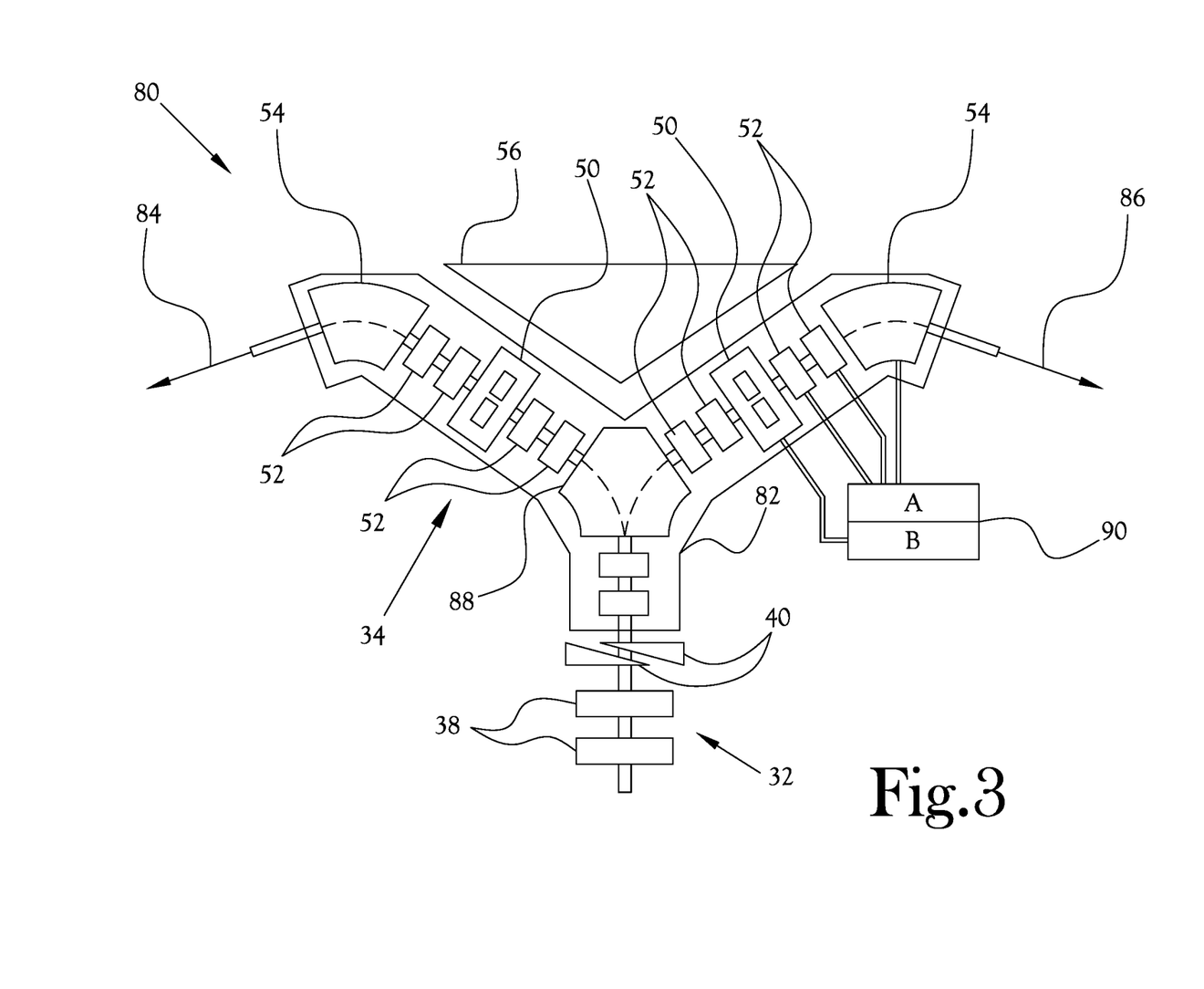
FIG. 3 illustrates a portion of a superconducting energy selection beamline according to still another example embodiment of the present general inventive concept.

FIG. 3 illustrates a portion of a superconducting energy selection beamline 80 according to still another example embodiment of the present general inventive concept. In this example embodiment, an achromatic bend 82 is configured so as to provide two proton beam pathways 84,86, so that the proton beam can be selectively delivered to two separate treatment rooms without rotating the achromatic bend 82. The achromatic bend 82 is configured in a generally Y-shape, and may be equipped with many of the same components as the achromatic bend 42 illustrated in FIG. 2. However, the achromatic bend 82 is configured with a superconducting dipole unit 88 that itself may be generally Y-shaped and configured with additional magnets to be electronically controlled so as to selectively deliver the proton beam to either one of the downstream paths in the achromatic bend 82. Thus, the proton beam can be changed between two treatment rooms by electronically controlling the superconducting dipole 88, rather than rotating the achromatic bend 82.

One of the challenges of the present general inventive concept, given the compact design and proximity of the collimator within the achromat, is to provide appropriate cooling paths to the collimator and magnets to maintain their respective operating temperatures, which can vary, for example, from approximately 50 degrees Kelvin for the collimator to approximately 4 degrees Kelvin for superconducting magnets. This challenge includes accurately maintaining temperatures of the components given that the heat transfer loads being applied to the magnets and collimator from the beam during operation can vary significantly. Example embodiments of the present general inventive concept can address this challenge by specifically configuring one or more refrigeration units to provide cooling paths to and/or from the collimator and magnets to achieve separate cooling paths. In some embodiments, a single refrigeration unit could be configured to embody multiple cooling stages so as to provide separate cooling paths to the collimator and the superconducting magnets, wherein one cooling path is in thermal communication with, or attached to, the magnets so as to cool the magnets to a working temperature of approximately 4 degrees Kelvin, and wherein another cooling path is in thermal communication with, or attached to, the collimator so as to cool the collimator to a working temperature of approximately 50 degrees Kelvin. In some embodiments, multiple refrigeration units could be configured to provide separate cooling paths to the collimator and magnets, respectively, so as to maintain the collimator and magnets at their respective, and significantly different, operating temperatures, in order to achieve accurate operational capability for the components as they operate in the high-heat beamline environment. Separate or independent cooling paths to the collimator and magnets can be configured to maintain different operating temperatures for the components and to help compensate for different heat loads on the components to increase accuracy of the beamline. For example, differences in cooling/heat transfer loads of the collimator and magnets can be configured to interact with beamline power and control mechanisms to increase accuracy of the beamline as the beamline travels along the beam path.

For example, as illustrated in the example embodiment of FIG. 3, a cooling or refrigeration unit 90 can be provided separately or within the achromatic bend to provide multiple one or more cooling paths to the magnets and collimator, respectively. The refrigeration unit 90 can be configured with separate or independent cooling stages A and B so as to provide separate or independent cooling paths to the magnets and collimator, respectively. As illustrated in FIG. 3, a cooling path is provided from the A cooling stage of the refrigeration unit to the magnets 54 and 52, and another cooling path is provided from the B cooling stage of the refrigeration unit 90 to the collimator 50. Multiple refrigeration units with separate or independent cooling stages could also be provided. In FIG. 3, only one refrigeration unit 90 is provided to one side of the achromat for convenience of illustration, but it is understood that such a unit could be provided be both side of the achromat, or provided a path to both sides, and so on.

Various example embodiments of the present general inventive concept may provide a proton treatment system including a proton accelerator structured to generate a proton beam, a beamline pathway configured to direct the proton beam from the proton accelerator to at least one treatment room, a bending magnet located in the beamline pathway and configured to bend the proton beam, and a collimator provided inside the bending magnet and configured to change the proton beam to a desired energy level. The bending magnet may be an assembly of superconducting magnets co-located in an outer vacuum chamber including, but not limited to, a first dipole configured at a proton beam entry point of the bending magnet, and a second dipole configured at a proton beam exit point of the bending magnet, wherein the collimator is configured between the first and second dipoles. The superconducting magnet assembly may further include a first pair of superconducting quadrupoles between the collimator and the first dipole, and a second pair of superconducting quadrupoles between the collimator and the second dipole. The collimator may be configured with a fixed aperture, and to be selectively installed in, and removed from, the bending magnet. The collimator may be configured with an adjustable aperture. The adjustable aperture may be an automated movable aperture configured with an iris mechanism, moving mandibles, or fluid constriction configuration. The collimator may be configured to receive a plurality of interchangeable apertures. The system may further include a degrader upstream from the bending magnet. The system may further include a pair of superconducting quadrupoles upstream from the bending magnet. The system may further include an initial collimator upstream from the bending magnet.

Various example embodiments of the present general inventive concept may provide a superconducting achromatic bend to be used in a proton therapy system, the superconducting achromatic bend including an outer vacuum chamber, and at least one collimator centrally located in a beamline inside the outer vacuum chamber. The superconducting achromatic bend may further include a first dipole configured at a proton beam entry point of the bending magnet, and a second dipole configured at a proton beam exit point of the bending magnet, wherein the collimator is configured between the first and second dipoles. The superconducting achromatic bend may further include one or more superconducting quadrupoles configured between the collimator and the first dipole, and one or more superconducting quadrupoles configured between the collimator and the second dipole.

Various example embodiments of the present general inventive concept may provide a proton treatment system, including a proton accelerator structured to generate a proton beam, a beamline pathway configured to direct the proton beam from the proton accelerator to at least one treatment room, a magnet assembly, including superconducting magnets, located in the beamline pathway and configured to transport the proton beam away from the accelerator into the at least one treatment room, an achromat, configured as an achromatic superconducting magnet assembly, that bends the proton beam away from the proton accelerator toward the at least one treatment room, and a collimator provided inside the achromat and configured to select the proton beam with the desired energy levels. The achromatic superconducting magnet assembly may include a first combination of superconducting dipole and quadrupole magnets configured at a proton beam entry point of the achromatic superconducting magnet assembly, and a second combination of superconducting dipole and quadrupole magnets configured at a proton beam exit point of the achromatic superconducting magnet assembly, wherein the collimator may be configured in the achromat between the first and second combinations of superconducting dipole and quadruple magnets. The collimator may be configured with a fixed aperture, and to be selectively installed in, and removed from, the achromat. The collimator may be configured with an adjustable aperture. The adjustable aperture may be an automated movable aperture configured with an iris mechanism, moving mandibles, or fluid constriction configuration. The collimator may be configured to receive a plurality of interchangeable apertures. The system may further include a degrader upstream from the achromat. The system may further include a pair of normal conducting or superconducting quadrupoles upstream from the achromat. The system may further include an initial collimator upstream from the achromat. The achromat may be configured to be rotated about an axis of rotation to selectively deliver the proton beam to a first treatment room or a second treatment room. The system may further include a rotation assembly configured to rotate the achromat so as to be selectively delivered to the first treatment room or the second treatment room.

Various example embodiments of the present general inventive concept may provide a superconducting achromatic bend to be used in a proton therapy system, the superconducting achromatic bend including an outer vacuum chamber containing a combination of dipole and quadrupole magnets, and at least one collimator centrally located in the combination of dipole and quadrupole magnets inside the outer vacuum chamber. The combination of dipole and quadrupole magnets may include a first combination of superconducting dipole and quadrupole magnets configured at a proton beam entry point of the combination of dipole and quadrupole magnets, and a second combination of superconducting dipole and quadrupole magnets configured at a proton beam exit point of the combination of dipole and quadrupole magnets, wherein the collimator is configured between the first and second combinations of superconducting dipole and quadrupole magnets.

Various example embodiments of the present general inventive concept may provide an achromatic superconducting magnet assembly to selectively bend a proton beam away from a proton accelerator toward first and second treatment rooms, including an outer vacuum chamber configured with a proton beam entry point, a first beam path leading to a first proton beam exit point, and a second beam path leading to a second proton beam exit point pointing in a direction different from the first proton beam exit point, and a bidirectional superconducting magnet unit configured proximate the proton beam entry point to selectively bend the proton beam to the first or second beam path, wherein each of the first and second beam paths include a first combination of superconducting dipole and quadrupole magnets configured to receive the proton beam from bidirectional the superconducting magnet unit, a second combination of superconducting dipole and quadrupole magnets configured to transmit the proton beam out of the achromatic superconducting magnet assembly, and a collimator configured between the first and second combinations of superconducting dipole and quadruple magnets and configured to select the proton beam with desired energy levels.

Various example embodiments of the present general inventive concept can be achieved by combining one or more of the features, functions, structures, devices, modules, and/or components described herein in any combination or sub-combination with one another, and it is contemplated by the inventors that such features, functions, structures, devices, modules and/or components can be constructed to be integrated or separate from one another, using known or later developed techniques in accordance with sound engineering judgment.

As described, the systems, apparatus, methods, processes, functions and/or operations for implementing the example embodiments of the present general inventive concept may be wholly or partially implemented in the form of apparatus that includes processing elements and sets of executable instructions. The executable instructions may be part of one or more software applications and arranged into software architecture. In general, embodiments of the present general inventive concept may be implemented using a set of software instructions that are designed to be executed by a suitably programmed processing element (such as a CPU, GPU (graphics processing unit), microprocessor, processor, controller, computing device, etc.). In a complex application or system such instructions are typically arranged into "modules" with each such module typically performing a specific task, process, function, or operation. The entire set of modules may be controlled or coordinated in their operation by an operating system (OS) or other form of organizational platform.

The application modules may include any suitable computer executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language. The computer-executable code or set of instructions may be stored in (or on) any suitable non-transitory computer-readable medium. In general, with regards to the embodiments described herein, a non-transitory computer-readable medium may include almost any structure, technology or method apart from a transitory waveform or similar medium.

As described, the systems, apparatus, methods, processes, functions, and/or operations for implementing the example embodiments of the present general inventive concept, such as but not limited to energy selection and/or rotation systems, may be wholly or partially implemented using, or in the form of, a set of instructions executed by one or more programmed computer processors such as a central processing unit (CPU) or microprocessor. Such processors may be incorporated in the circuitry and components of an apparatus, server, client or other computing or data processing device operated by, or in communication with, other components of the system.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components, processes or functions described in this application may be implemented as software code to be executed by a processor using any suitable computer language such as, for example, Java, JavaScript, C++ or Perl using, for example, conventional or object-oriented techniques. The software code may be stored as a series of instructions, or commands in (or on) a non-transitory computer-readable medium, such as a random-access memory (RAM), a read only memory (ROM), a magnetic medium such as a hard-drive or a floppy disk, or an optical medium such as a CD-ROM. In this context, a non-transitory computer-readable medium is most any medium suitable for the storage of data or an instruction set aside from a transitory waveform. Any such computer readable medium may reside on or within a single computational apparatus, and may be present on or within different computational apparatuses within a system or network.

According to some example implementations, the term processing element or processor, as used herein, may be a central processing unit (CPU), or conceptualized as a CPU (such as a virtual machine). In such example implementation, the CPU or a device in which the CPU is incorporated may be coupled, connected, and/or in communication with one or more peripheral devices such as the movement mechanisms, as well as one or more displays. In other example implementations, the processing element or processor may be incorporated into a mobile computing device, such as a smartphone or tablet computer.

The non-transitory computer-readable storage medium referred to 15 herein may include a number of physical drive units, such as a redundant array of independent disks (RAID), a floppy disk drive, a flash memory, a USB flash drive, an external hard disk drive, thumb drive, pen drive, key drive, a High-Density Digital Versatile Disc (HD-DVD) optical disc drive, an internal hard disk drive, a Blu-Ray optical disc drive, or a Holographic Digital Data Storage (HDDS) optical disc drive, synchronous dynamic random access memory (SDRAM), or similar devices or other forms of memories based on similar technologies. Such computer readable storage media allow the processing element or processor to access computer-executable process steps, application programs and the like, stored on removable and non-removable memory media, to off-load data from a device or to upload data to a device. As mentioned, with regards to the embodiments described herein, a non-transitory computer-readable medium may include almost any structure, technology or method apart from a transitory waveform or similar medium.

Certain implementations of the disclosed technology are described herein with reference to block diagrams of systems, and/or to configurations, functions, processes, or methods. It will be understood that one or more of the configurations, methods, processes, and functions can be implemented by computer-executable program instructions. Note that in some embodiments, one or more of the configurations, methods, processes, and functions may not necessarily need to be performed in a particular order, or may not necessarily need to be performed at all.

These computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods described herein. These computer program instructions may also be stored in a computer-readable memory that can direct a computer or other programmable data processing apparatus to function in a specific manner, such that the instructions stored in the computer-readable memory produce an article of manufacture including instruction means that implement one or more of the functions, operations, processes, or methods described herein.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. An achromatic superconducting magnet assembly to selectively bend a proton beam away from a proton accelerator toward first and second treatment rooms, comprising:
   an outer vacuum chamber configured with a proton beam entry point, a first beam path leading to a first proton beam exit point, and a second beam path leading to a second proton beam exit point pointing in a direction different from the first proton beam exit point; and
   a bidirectional superconducting magnet unit configured proximate the proton beam entry point to selectively bend the proton beam to the first or second beam path;
   wherein each of the first and second beam paths comprise:
   a first combination of superconducting dipole and quadrupole magnets configured to receive the proton beam from bidirectional the superconducting magnet unit,
   a second combination of superconducting dipole and quadrupole magnets configured to transmit the proton beam out of the achromatic superconducting magnet assembly, and
   a collimator configured between the first and second combinations of superconducting dipole and quadruple magnets and configured to select the proton beam with desired energy levels.

2. The assembly of claim 1, wherein the superconducting magnet unit is configured to be selectively rotated so as to selectively bend the proton beam to the first beam path or the second beam path.

3. The assembly of claim 1, further comprising one or more refrigeration units configured to provide one or more separate cooling paths to and/or from the collimator and the first combination and/or second combination of superconducting dipole and quadruple magnets.

* * * * *